United States Patent [19]
Weijand et al.

[11] Patent Number: 5,948,004
[45] Date of Patent: Sep. 7, 1999

[54] IMPLANTABLE STIMULATOR HAVING AN EFFICIENT OUTPUT GENERATOR

[75] Inventors: Koen J. Weijand, Hoensbroek; Robert Leinders, Limbricht, both of Netherlands

[73] Assignee: Medtroni, Inc., Minneapolis, Minn.

[21] Appl. No.: 08/915,677

[22] Filed: Aug. 21, 1997

[51] Int. Cl.⁶ ..................................................... A61N 1/362
[52] U.S. Cl. ................................................. 607/9; 607/72
[58] Field of Search ............................ 67/5, 9, 68, 72–74

[56] References Cited

U.S. PATENT DOCUMENTS 4,031,899  6/1977  Renirie .
4,768,512  9/1988  Imran .

*Primary Examiner*—William E. Kamm
*Assistant Examiner*—George R. Evanisko
*Attorney, Agent, or Firm*—Michael J. Jaro; Harold Patton

[57] ABSTRACT

An output pulse generator is provided which is particularly suitable for implantable medical simulators, such as cardiac pacemakers, where there is a high premium on efficient energy transfer from the battery source to the output load. A plurality of relatively small size output capacitor are utilized in combination with a switching circuit for alternately charging respective capacitors and then discharging them through the load in such a manner that there is always one capacitor providing a substantially constant output voltage while at least one other capacitors is being recharged. Different combinations of switching networks are used to provide programmable output voltage levels. The use of relatively small capacitors, e.g., in the range of 0.1–0.5 F, along with a relatively high drive frequency, e.g., 32 kHz, enables substantially continuous transfer of energy from the battery to the capacitors only during the time of pulse output, and high efficiency generation of a stimulus pulse with a substantially constant voltage level throughout the pulse duration. Variation of the drive frequency is done in order to adjust the generated pulses to the output load.

30 Claims, 5 Drawing Sheets

IMPLANTABLE STIMULATOR HAVING AN EFFICIENT OUTPUT GENERATOR

FIELD OF THE INVENTION

This invention lies in the field of voltage adjustable output generators and, more particularly, output generators for use in implantable stimulators and which provide efficient energy transfer from a battery supply to a load.

BACKGROUND OF THE INVENTION

There remains a great need to efficiently generate programmable voltage pulses for delivery to a patient location from an implanted device, e.g., to deliver pacing pulses from an implanted pacemaker to a patient's heart. The generation of stimulus pulses has remained the subject of continuing research and development, largely because the efficiency of generation is a primary determinant of energy expenditure, and thus of device longevity. Battery development has been ongoing, but so too have been the demands on the implanted device for extra features such as telemetry capability, processing and storage of diagnostic data, performing various logic functions, etc. With the increasing demands for performance capabilities, and of course longevity, improving the efficiency of delivering the periodic stimulus pulses remains a major goal, for implantable medical devices in particular.

The conventional prior art circuit used in an implantable device such as a pacemaker, defibrillator, nerve stimulator, etc., utilizes one or more large storage capacitors which are discharged to the load through a coupling capacitor to provide the stimulus pulse, the storage capacitor or capacitors then being recharged between pulses. In a pacemaker, such storage capacitors are typically in the range of 10–22 F; such a large capacitor occupies an undesirably large volume, is expensive, and is relatively inefficient to recharge. In older circuits, in order to provide a programmable voltage output, a single large storage capacitor was pumped to a programmable value with small capacitors. However, such an arrangement had the disadvantage that the voltage value could not be changed quickly. Subsequently, a next system was developed where several large capacitors, each charged to the battery voltage or half battery voltage, were stacked during the pulse duration so as to provide the programmed voltage output value. However, in this situation, the effective capacitance during pulse delivery, and thus the output impedance, is a variable, depending on the programmed output voltage value. Further, stacking of capacitors results in a smaller effective capacitance, such that there is increased voltage reduction while current flows to the load, making it more difficult to maintain a long pulse width without a sagging pulse voltage level. Further, and importantly, efficiency is compromised, due to the need to recharge significantly.

There thus remains a significant need in the implantable device art for an improved output generator which can provide more efficient delivery of energy to the target location, and also meet the other demands of a modern device. For example, such an improved energy efficient output generator must also be programmable to deliver stimulus pulses at different output levels. It is a further object to provide, in a battery-driven device, an efficient voltage pulse generator, where the voltage level of the pulse is maintained substantially constant, e.g., within 10% for the duration of the pulse.

SUMMARY OF THE INVENTION

There is provided an output circuit for generating programmable voltage stimulus pulses, for use in an implantable device such as a cardiac pacemaker, nerve stimulator, and the like. The output circuit meets the above objects of efficient generation of voltage pulses and programmable voltage levels, and further avoids the need of a set of large output capacitors.

In accord with these objects, there is provided a voltage pulse generator for use with an implantable device such as a pacemaker, or other device powered by a battery source. The generator has a pair, or plural pairs of small capacitors, e.g., less than 10 F, in combination with a switching circuit operative during the stimulus pulse duration to alternately switch one or more of the small capacitors to receive energy from the battery source and then to deliver energy to the load, e.g., the heart for a pacemaker application; another capacitor, or capacitors, are switched in an inverse or alternate manner, such that at all times one or more capacitors are receiving energy from the battery source while the others are delivering energy to the load. The switching circuit is driven at a high rate, e.g., 32 kHz, such that during the pulse duration the small capacitors do not discharge very much, and energy is delivered from the battery source at a substantially constant rate. The switching circuit switches at least one capacitor that is delivering energy to the load only when at least another capacitor, which has been charging, is switched to the load, thereby providing overlapping of the connection to the output, resulting in a substantially constant voltage pulse.

In a first simplest embodiment, only two capacitors are used. The switching circuit is driven by a high frequency signal, at a rate that is high compared to the duration of the pulse to be delivered. During the pulse duration, the switching circuit alternately switches a first capacitor to be charged from the battery source while the second is delivering energy to the load; and then switches the first capacitor to deliver energy to the load while the second is being re-charged from the battery source. Circuitry provides that there is always a capacitor connected to the output, in an overlapping fashion.

In a more complex embodiment that enables programming of the voltage level, two or more pairs of such small capacitors are used. For example, for a two pair output circuit, a first pair can be connected to act as an effective first capacitance, while the second pair acts as an effective second capacitance. The switching circuit additionally acts to switch the connection of each pair of capacitors, i.e., to series or parallel, thereby changing the output voltage level. Thus, if each pair is charged across the battery in parallel, and then discharged across the load in series, the output voltage is double the battery voltage; if each pair is charged in series and then discharged in parallel, the output pulse voltage is half the battery voltage. Additional voltage levels can be obtained by different combinations of capacitors, without limit. In a device such as a programmable pacemaker, the voltage level can be programmed from an external source, providing the data for controlling the switching combinations.

BRIEF DESCRIPTION OF THE DRAWINGS

1D is a series of timing diagrams illustrating the drive signal for driving each of the two capacitors, and showing the composite output pulse with duration D.

DESCRIPTION OF THE PREFERRED EMBODIMENTS

Figure 1A:
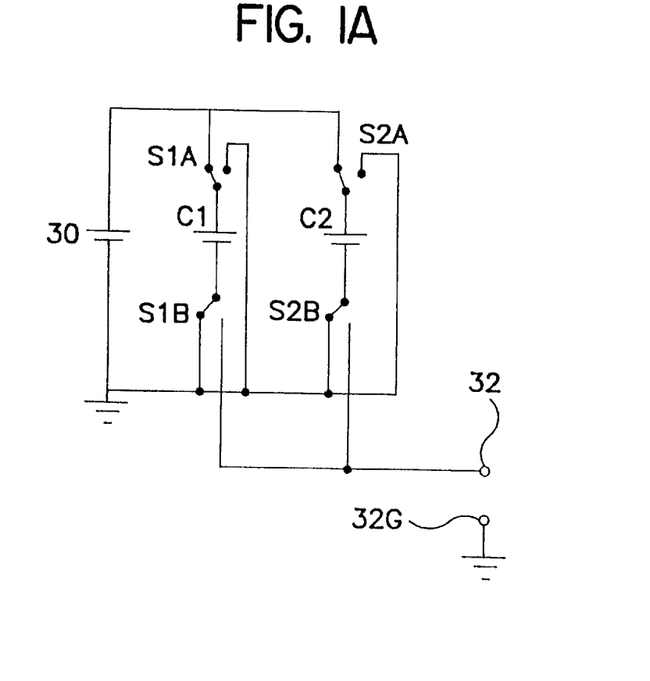
FIG. 1A is a simplified circuit diagram of a two capacitor embodiment, illustrating both capacitors connected to the battery, as is the condition when no output pulse is being generated.

Referring now to FIGS. 1A–1D, there is illustrated a simple 2-capacitor output circuit in accordance with this invention, for providing an output stimulus pulse having a magnitude equal to the battery voltage. The battery 30 is shown in circuit together with capacitors C1 and C2; and switches S1A and S1B for switching the circuit connection of C1, and switches S2A and S2B for switching the circuit connection of the C2. The switches are preferably low impedance, low loss FET switches, as are commercially available. In FIG. 1A, both capacitors are switched into direct connection across battery 30, so that both capacitors are charged. Suitably this is the switching connection when a pulse is not being delivered; as a result, no power is being transferred to the capacitors when no stimulus pulse is being generated. Battery may be of any desired design as discussed below and broadly functions as an energy supply or source.

Figure 1B:
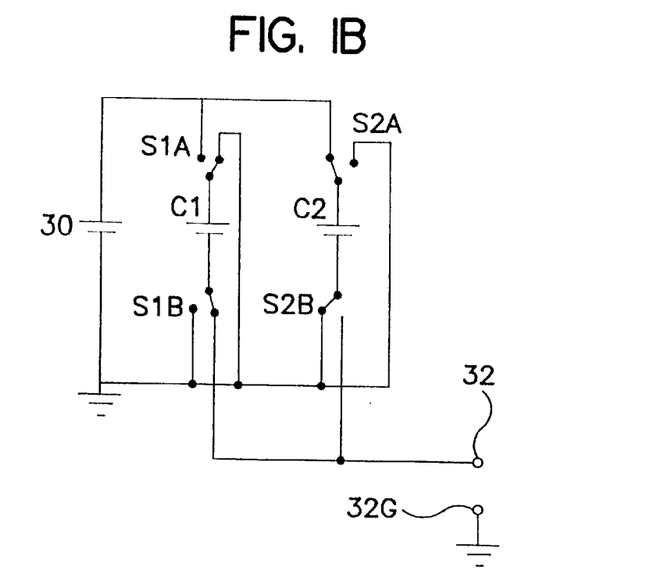
FIG. 1B is the same circuit as in FIG. 1A, but illustrated with a first capacitor being connected across the circuit output while the second capacitor is connected across the battery.
Figure 1C:
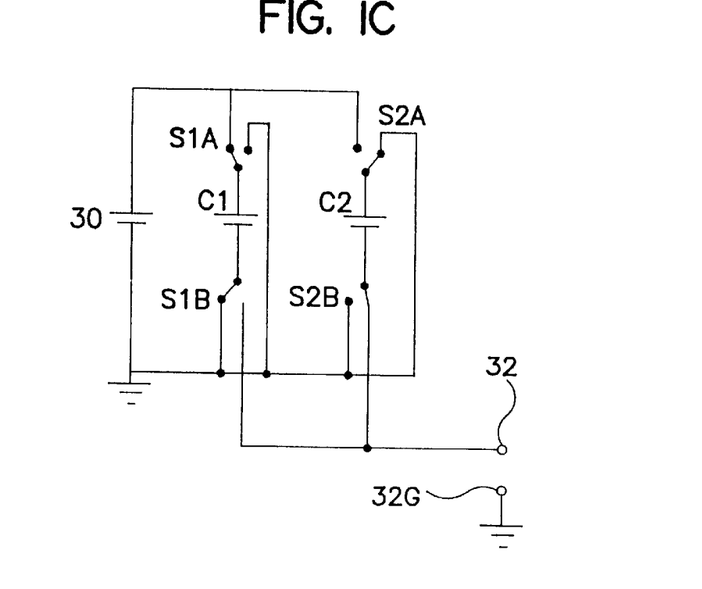
FIG. 1C is the same circuit, illustrated with the second capacitor connected across the circuit output while the first capacitor is connected across the battery; and FIG.
Figure 1D:
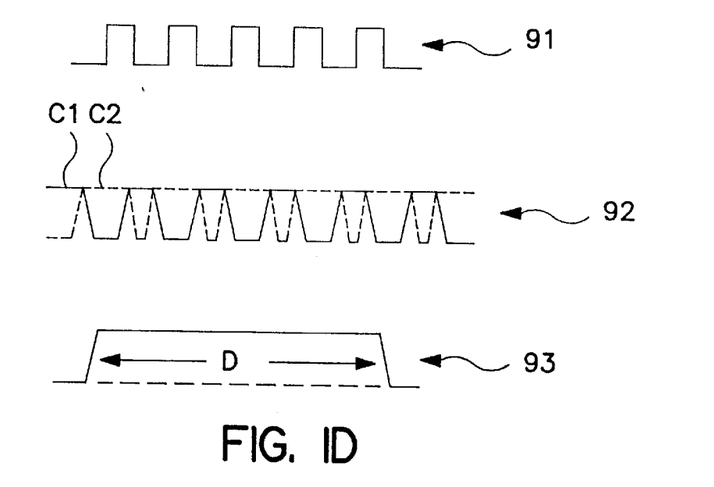

In FIG. 1B, in accordance with a drive signal illustrated in FIG. 1D, capacitor C2 remains connected across battery 30, but capacitor C1 is switched so that it is connected across the output terminals illustrated as 32, 32G.

FIG. 1C shows the alternate switching arrangement, at which point the switching circuit is adjusted so that capacitor C1 is connected across battery 30, while capacitor C2 is connected across the output terminals. Thus, comparing the connections of FIGS. 1A and 1B, it is seen that each capacitor is alternately switched between a connection where it is receiving energy from the battery 30, and then a connection where it is delivering energy to the output; and each capacitor is in an alternate switching phase from the other, i.e., when one is charging the other is discharging to the load, and vice-versa. The newer chemistry batteries, such as LiMnO2, LiVnO5, etc. are suitable for the output circuit of this invention.

Referring to FIG. 1D, the upper timing diagram 91 illustrates a high frequency drive signal. As used herein, high frequency means that the period of the drive signal is small compared to the duration D of the output pulse, the latter being illustrated in the lower timing diagram of FIG. 1D. In practice, the output stimulus 93 may have a duration D of about 1 ms, while the drive signal may suitably have a rate of 32 kHz. For these typical figures, there would be thirty-two cycles of the drive signal during the duration D, such that each cycle of the drive signal has a time period which is only a bit more than 3% of the pulse duration. Thus, a single capacitor connection is only about 1.5% D, while the interleaving of two sets of capacitors is about 3% D. The switch frequency can be controlled to minimize rate, and thus switching losses, as a function of the required load current. For greater load currents during the pulse, the rate must be higher, so as to avoid capacitor discharge; but for lower load currents, lower switching rates can be used.

As illustrated in the second, or middle timing diagram 92 of FIG. 1D, the basic timing signal is processed to provide different signals illustrated as driving the switches connected to capacitors C1 and C2 respectively, such that they are driven alternately, as described above. In this manner, substantially all of the energy is delivered to the load during a stimulus pulse; energy is transferred from the battery to the respective capacitors during the pulse, and is transferred at substantially a constant rate. In each cycle of the drive signal a small portion of the pulse energy is delivered first to capacitor C1 and then to capacitor C2. This is repeated a large number of times during the pulse. After termination of the pulse, with both capacitors connected across the battery, no energy is transferred to the capacitors after they are charged. Since the capacitors need only hold a small portion of the pulse energy at any time, they can be relatively small. Such small sized capacitors suitably have values less than 10 F, e.g., about 1 F or less; and preferably have values no greater than 0.5 F.

It is noted that a discharged capacitor is inefficient to recharge. A general rule of thumb is that the efficiency of recharging a capacitor is 50% of the relative voltage difference before recharging. If the capacitors are discharged to 90% of the previously stored value, the recharge is accomplished with about 95% efficiency. It is thus seen that the switching rate must be high enough to prevent too much discharge, in order to provide a high efficiency circuit with small sized capacitors. For example, assume a load current of 10 mA, a 0.5 F capacitor, and a discharge/charge time of 15 microseconds (corresponding to a rate of 33.33 kHz). This results in a drop in capacitor voltage of 300 mV, e.g., from 3 V to 2.7 V during discharge; during recharge from 2.7 V back to 3 V, the efficiency is 95%. A smaller capacitor or lower rate could be used, at sacrifice of efficiency. However, a preferred design of a generator circuit in accord with this invention provide for an output pulse that varies no more than about 85–95% during the pulse duration, with a recharge efficiency greater than 90%.

Figure 3:
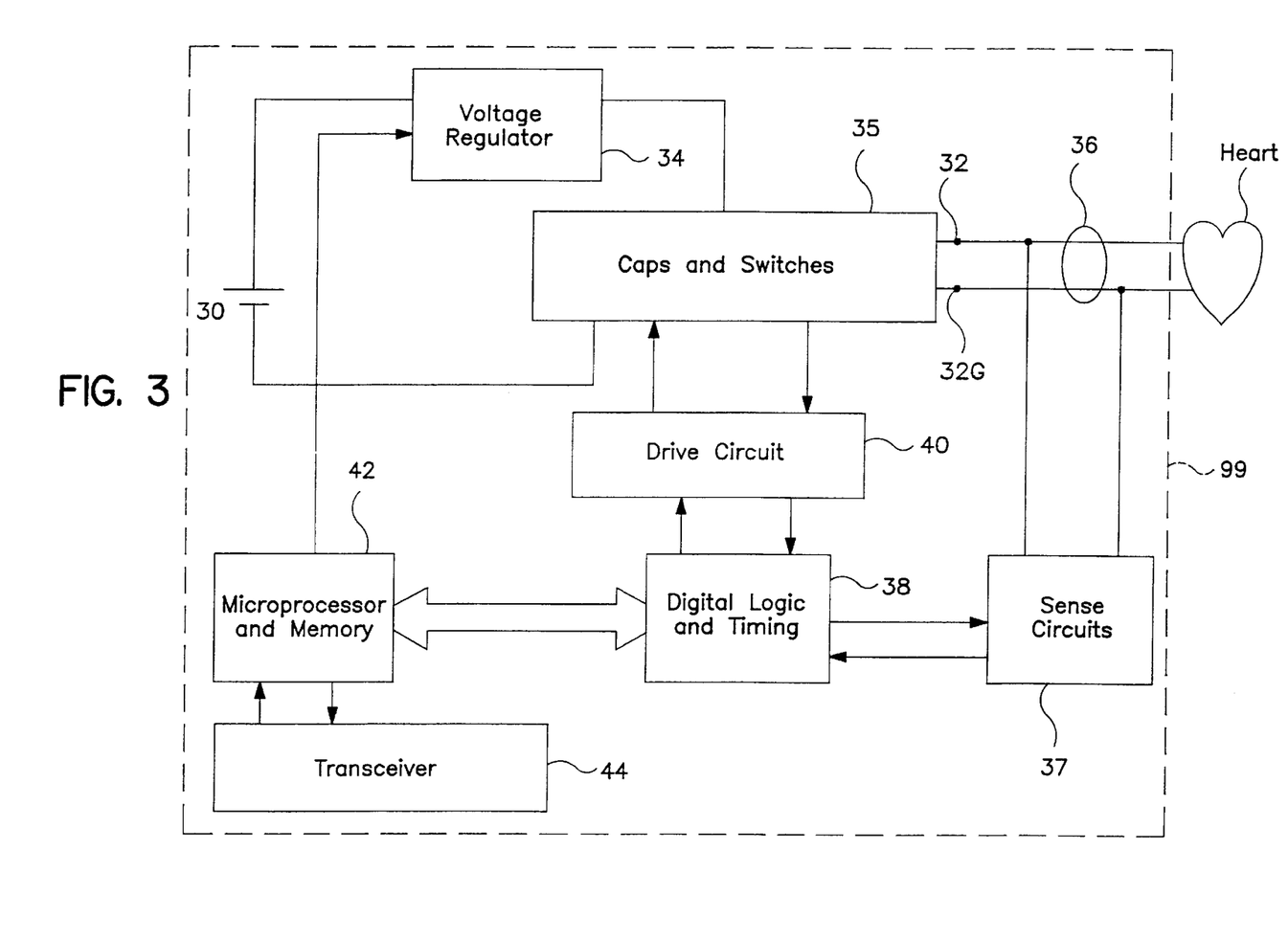
FIG. 3 is a block diagram of a pacemaker having a voltage generator circuit according to this invention.

In a further aspect of the invention, the drive signals to the switches provide that there is always one capacitor connected to the output terminals, i.e., the capacitors are connected in an overlapping fashion. Drive circuit 40, illustrated in FIG. 3, provides the feedback for accomplishing this. In practice, the switches are suitably FETs, and by monitoring the gate voltage of each switch and feeding this gate voltage signal into the control logic, an inherently safe and cross-current-free operation is easily obtained, that is independent of parasitic influence and power supply variations. Thus, the logic only turns off one FET when the alternate, or complementary FET is turned on, as confirmed by the feedback.

Figure 2A:
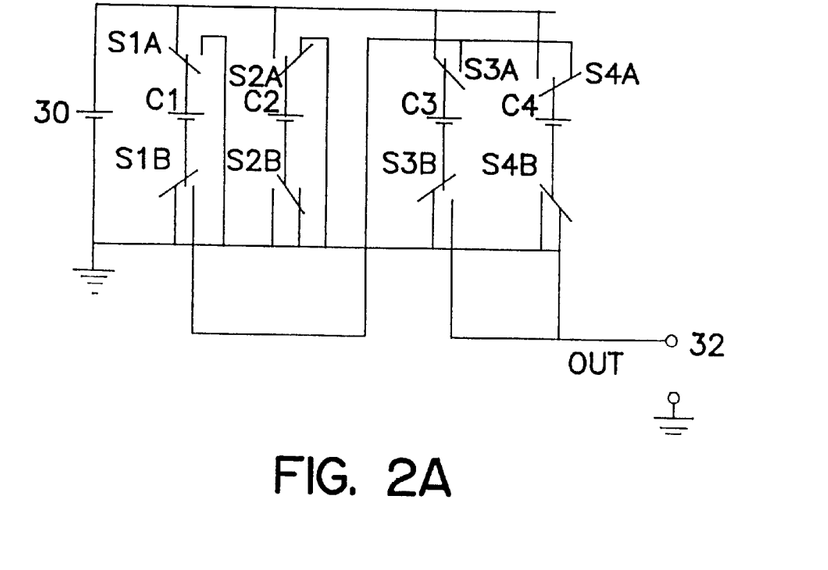
FIGS. 2A–2B illustrate a four capacitor output circuit in accord with this invention for generating a voltage output pulse having a magnitude of two times the battery voltage.
Figure 2B:
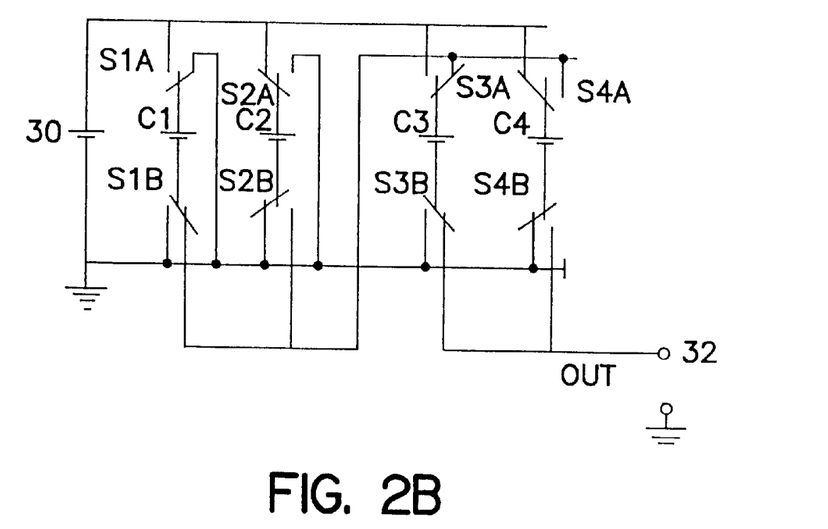

Referring to FIGS. 2A and 2B, there are illustrated switching arrangement for the first half and second half respectively of a drive cycle, for providing a pulse output of value $2V_B$. The switching circuit comprises four pairs of switches, S1A, S1B; S2A, S2B; S3A, S3B; S4A; S4B. In FIG. 2A, a switching arrangement is illustrated showing capacitors C1 and C3 being charged in parallel, while capacitors C2 and C4 are discharging in series between the output terminals. In FIG. 2B, the second half of the drive signal cycle, the arrangements are reversed, i.e., capacitors C2 and C4 are being charged in parallel directly across the battery 30, while capacitors C1 and C3 are connected in series across the output terminals. The result of this switching arrangement is that during a first half cycle, one pair of capacitors is charged to the battery voltage $V_B$, while the other pair of capacitors is placed in series, producing a voltage of $2V_B$ across the load; during the next half cycle of the drive signal, the capacitors that had been charged are switched so that they are connected in series, while the capacitors that had been delivering energy are placed across the battery to recharge. By connecting the capacitors that are switched across the load in series, each contributes a voltage of $V_B$, thus producing a doubled output voltage.

Figure 2C:
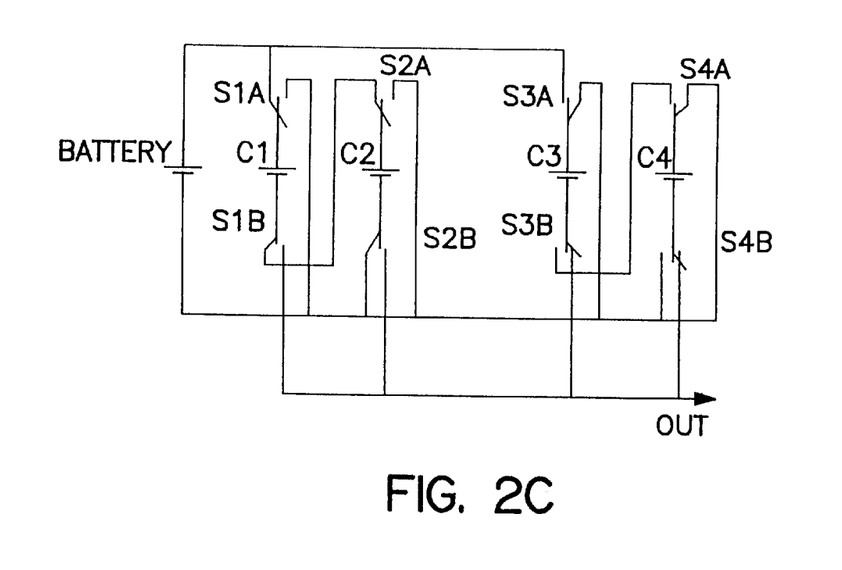
FIGS. 2C and 2D show a circuit with alternate switching arrangements for generating a voltage output pulse having an output magnitude of one-half the voltage battery.
Figure 2D:
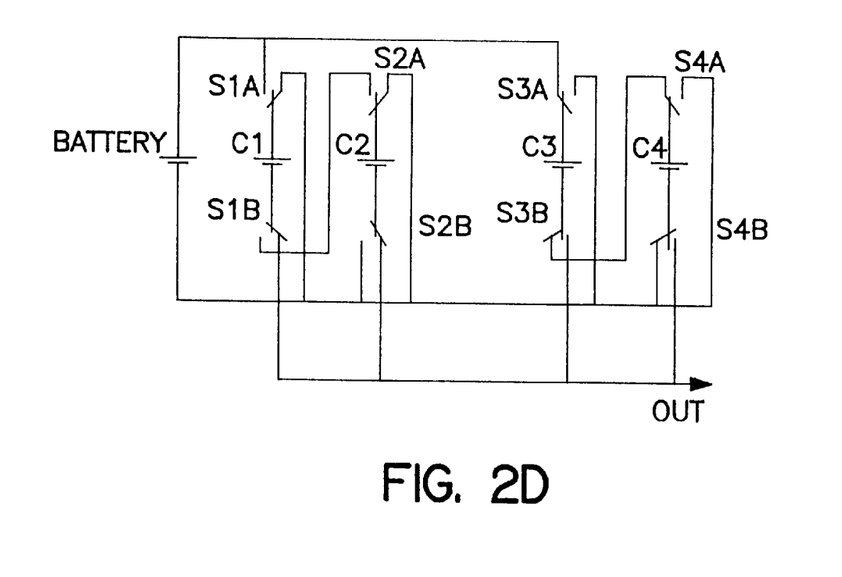

Referring to FIGS. 2C and 2D, there are shown alternate switching arrangements for first and second half-cycles, respectively of a drive cycle, for providing a pulse output of one-half $V_B$. Thus, in FIG. 2C, C1 and C2 while C3 and C4 are connected in parallel across the load. During the next half cycle, illustrated in FIG. 2D, C1 and C2 are connected in parallel across the load, while C3 and C4 are charged in series.

It is to be understood that additional and more complex switching arrangements can be routinely made within the scope of this invention. Thus, any combination of capacitor pairs and appropriate switching can be utilized to provide different voltage levels. Also, it is to be understood that the capacitors can be switched in different manners within the duration D of the pulse, e.g., a pulse can be provided to give an output ½ $V_B$ for a first fraction of the duration; level $V_B$ for a second fraction; level 2B for a third fraction, etc.

Referring now to FIG. 3, there is shown a circuit block diagram of an exemplary pacemaker device using the voltage output circuit of this invention. Pacemaker is of a conventional design an features a hermetic enclosure 99 as is well known in the art, inside of which the various components are housed. The capacitor and switching combination, containing two or more capacitors, is illustrated in block 35. It may be connected through a voltage regulator 34, to battery 30, where voltage regulator 34 can be controlled to vary the amount of voltage received by the capacitors, thereby providing further adjustment of the pulse output level. The voltage regulator may also be inserted in series with the load, in a known manner. As shown, the output terminals 32, 32G are connected through a conventional pacemaker lead 36 to the heart. Signals received from the heart are connected to sense circuits 37, for generating signals representative of heart activity. The sense signals are transmitted to digital logic and timing circuit 38, which provides conventional pacemaker logic and timing functions. Of particular importance to this invention is the determination of the timing of delivery of an output stimulus. Thus, when a stimulus is called for, a signal is transmitted from block 38 to drive circuit 40, for generation of the drive signals which switch the switches illustrated in FIGS. 1A–1C and FIGS. 2A–2D. Logic and timing circuit 38 is interconnected with a microprocessor and suitable memory illustrated at 42, providing software control. Block 42 in turn is interconnected with transceiver 44, which can receive programming data and instructions from an external programmer, all as is well known in the pacemaker art. Thus, the change in stimulus duration D, or desired output voltage level, may be downloaded through transceiver 44 into the memory portion of 42, and used in generating the drive circuit signals which switch the output generator. Likewise, the rate of the device signal can be reprogrammed, to correspond to the effective load being driven by the pulses.

There is thus provided a highly efficient battery-driven pulse generator, capable of being programmed to different voltage output values. Although a preferred embodiment for the circuit of the invention is an implantable pacemaker or other type of implantable stimulator, it is particularly applicable for any use where high efficiency is desirable, and/or avoidance of large output capacitors is important. Moreover, while illustrated in the context of a battery driven device, the present invention may be utilized in an environment in which low power is a consideration. The invention replaces a circuit with a set of large capacitors by a set of small capacitors pumped at a high frequency. The capacitors can be implemented in an array, e.g., where 4 or 8 small sized capacitors occupy the same volume as one 22 F capacitor. The resulting output pulse has a ripple at a pumping, or drive frequency, providing an amplitude envelope that is flatter than that of the conventionally produced capacitor-discharge pulse.

While the present invention has been described in detail with particular reference to a preferred embodiment and alternate embodiments, it should be understood variations and modifications can be effected within the scope of the following claims. Such modifications may include substituting elements or components which perform substantially the same function in substantially the same way to achieve substantially the same result for those described herein.

What is claimed is:

1. An output circuit in an implantable device comprising:
   a hermetic enclosure, the hermetic enclosure containing an energy source;
   a source circuit for providing power from the energy source, the source circuit housed within the hermetic enclosure;
   at least two small size output capacitors housed with the hermetic enclosure;
   an output circuit adapted to be connected to the load, the output circuit housed within the hermetic enclosure;
   pulse means for providing a pulse signal having a predetermined pulse duration, the pulse means housed with the hermetic enclosure; and
   switching means housed with the hermetic enclosure, the switching means enabled by the pulse signal for the pulse duration, for alternately switching each said capacitor into a circuit with the output circuit and into a circuit with the source circuit wherein during the pulse duration at least one of the capacitors is substantially always delivering power to the load.

2. The circuit as described in claim 1, wherein the switching means comprises a high frequency drive means for switching the capacitors at a high rate relative to the pulse duration, whereby each said capacitor is alternately switched to receive energy from the energy source a plurality of times during each said pulse duration and to deliver energy to the load a plurality of times during each said pulse duration.

3. The circuit as described in claim 2, wherein the at least two capacitors comprise two capacitors, and wherein the switching means cyclically connects a first of the at least two capacitors to the source circuit to receive energy from the energy source while connecting the second of the at least two capacitors to the output circuit to deliver energy to the load, and then alternately connects the first capacitor to the output circuit while connecting the second capacitor to the source circuit.

4. The circuit as described in claim 2, wherein the at least two capacitors comprises at least two pairs of capacitors, and wherein the switching means has means for switching each said pair of capacitors to alternately be connected to the source circuit and to the output circuit wherein during the pulse duration at least one of the capacitor pairs is substantially always delivering power to the load.

5. The circuit as described in claim 4, comprising level control means for controlling the switching means wherein the switching means may be controlled so as to produce a predetermined output pulse level.

6. The circuit as described in claim 2, wherein the drive means comprises a drive oscillator producing a drive signal at a rate of up to at least 32 kHz.

7. The circuit as described in claim 6, wherein the drive oscillator further comprises a rate controllable drive oscillator.

8. The circuit as described in claim 1, wherein the switching means comprises at least one switch connected to each said capacitor, and comprising feedback control means for controlling that at least one of the capacitors is always connected to the output circuit in an overlapping fashion.

9. The circuit as described in claim 1, wherein the capacitors have values no greater than about 0.5 F.

10. An implantable stimulus apparatus having an output circuit, in combination with an energy supply, for delivering stimulus pulses to a load, the output circuit further comprising:

capacitive storage means for storing energy;

pulse timing means for generating pulse timing signals, each said pulse timing signal having a predetermined pulse duration;

first transfer means operative substantially only during each said pulse duration for transferring energy from the energy supply to the storage means at a substantially constant rate during the duration; and second transfer means operative for transferring energy from the capacitive storage means to the load during each said pulse duration, wherein the second transfer means delivers a stimulus pulse during each said pulse duration, with substantially all of the energy delivered to the load during each stimulus pulse being transferred from the energy supply during the duration of the each pulse.

11. The apparatus as described in claim 10, wherein the capacitive storage means comprises a plurality of small capacitors.

12. The apparatus as described in claim 11, wherein the capacitive means comprises first and second capacitors, and the first transfer means comprises first switching means for alternately switching the first and second capacitors to the energy source.

13. The apparatus as described in claim 12, wherein the second transfer means comprises second switching means for switching the second capacitor to the load when the first capacitor is switched to the energy source, and for switching the first capacitor to the load when the second capacitor is switched to the energy source.

14. The apparatus as described in claim 13, comprising a high frequency drive circuit for driving the first and second transfer means, wherein the switching rate of the first and second transfer means is high relative to the pulse duration.

15. The apparatus as described in claim 11, wherein the capacitive means comprises a plurality of pairs of capacitors, and further comprising a level means for connecting each said pair of capacitors so as to control the output voltage of each said delivered pulse.

16. The apparatus as described in claim 11, wherein the second transfer means comprises means for continually transferring energy from at least one of the capacitors during the pulse duration, whereby a continuous pulse is delivered to the load.

17. An implantable pacemaker for generating pace pulses, comprising an energy source, control means for generating pace pulse control signals, the signals having a predetermined pulse duration corresponding to the timing of each said pace pulse, and output means for generating the pace pulses under control of the control signals, the output means further comprising:

at least two capacitors;

output terminals, the output terminals outputting a pacing pulse, the output terminals coupled to the at least two capacitors;

a drive generator for generating a drive signal having a cycle period less than the duration; and switching circuit means enabled during each said pulse duration for switching a first of the capacitors to the energy source and a second of the capacitors to the output terminals during a first portion of each said drive cycle period and alternatingly switching the second of the capacitors to the energy source and the first of the capacitors to the output terminals during a second portion of each said drive cycle period, wherein during the pulse duration an output is provided to the output terminals alternately by the first and second capacitors.

18. The pacemaker as described in claim 17, wherein the switching circuit means comprises overlap means for switching the capacitors whereby one of the capacitors is always switched across the output terminals.

19. The pacemaker as described in claim 17, wherein the drive generator has an oscillator circuit which produces the drive signal with a small cycle period relative to the duration.

20. An output circuit for an implantable stimulator having a hermetic enclosure, comprising:

an energy source;

a drive circuit for producing a high frequency switching signal, the drive circuit coupled to the energy source;

first and second sets of capacitors, said capacitors coupled to the energy source;

output terminals, said output terminals coupled to said capacitors; and switching means for switching the sets of capacitors in an alternating manner wherein the first set is charged by the energy source while the second set is connected to the output terminals, and the second set is charged by the energy source while the first set is connected to the output terminals.

21. The output circuit as described in claim 20, wherein the switching means comprises overlap means for controlling the switching of each said set of capacitors alternately with the energy source and the output terminals during each cycle period of the switching signal in an overlapping manner wherein the connection of the respective sets to the output terminals overlap and provide a substantially constant output voltage at the output terminals.

22. The output circuit as described in claim 21, comprising feedback means for switching one set of capacitors in circuit with the energy source only when the other set of capacitors is switched in circuit with the output terminals.

23. The output circuit as described in claim 20, wherein each of the sets comprises one capacitor.

24. The output circuit as described in claim 20, wherein each of the sets comprises two capacitors.

25. The output circuit as described in claim 24, further comprising set switching means for switching the connection of the two capacitors in each said set, and program means for programming the connection so as to provide a predetermined output voltage.

26. The output circuit as described in claim 20, further in combination with pulse control means for controlling the switching means to operate at a predetermined rate and with a predetermined pulse duration, thereby providing output pulses from the output terminals at the rate and with the duration.

27. A device for providing an output pulse of substantially constant voltage for delivery to a load, comprising:

an energy source;

a set of small sized capacitors;

pulse means for defining a pulse to be generated, the pulse having a duration;

transfer means operative during the duration for cyclically discharging energy from the capacitors to the load and for re-charging the capacitors from the energy source at a rate permitting the capacitors to discharge no more than about 85%–95%, the transfer means also having connecting means for connecting at least one of the capacitors to discharge energy to the load at all times during the pulse duration and producing an output pulse with a voltage that varies by no more than about 85–95% during the duration.

28. The device as described in claim 27, wherein the transfer means comprises drive signal means for generating a cyclical drive signal having a cycle period much less than the pulse duration and permitting the capacitors to be discharged and re-charged during the duration at a rate where the efficiency of re-charging the capacitors is greater than 90%.

29. The device as described in claim 27, further comprising overlap feedback means for disconnecting one of the capacitors from being connected to discharge energy to the load only when another of the capacitors is connected to discharge energy to the load.

30. The device as described in claim 27, further comprising drive means for switching each of the capacitors alternately into connection with the load and into connection with the energy source at an adjustable rate, and rate control means for adjusting the rate as a function of the level of the load.

* * * * *

UNITED STATES PATENT AND TRADEMARK OFFICE
CERTIFICATE OF CORRECTION

PATENT NO. : 5,948,004
DATED : September 7, 1999
INVENTOR(S) : Koen J. Weij and Robert Leinders It is certified that error appears in the above-identified patent and that said Letters Patent is hereby corrected as shown below:

Cover Page, Item 73 Assignee: "Medtroni" should be "Medtronic"

Signed and Sealed this

Fifth Day of December, 2000

Attest:

Q. TODD DICKINSON

*Attesting Officer*  *Director of Patents and Trademarks*